(12) United States Patent
Hung (10) Patent No.: US 10,653,865 B2
(45) Date of Patent: May 19, 2020

(54) MANUAL VENOUS CATHETER ASSEMBLY

(71) Applicant: Chih-Hua Hung, Hsinchu (TW)

(72) Inventor: Chih-Hua Hung, Hsinchu (TW)

(*) Notice: Subject to any disclaimer, the term of this patent is extended or adjusted under 35 U.S.C. 154(b) by 277 days.

(21) Appl. No.: 15/572,403

(22) PCT Filed: May 8, 2015

(86) PCT No.: PCT/CN2015/000118
§ 371 (c)(1),
(2) Date: Nov. 7, 2017

(87) PCT Pub. No.: WO2016/179719
PCT Pub. Date: Nov. 17, 2016

(65) Prior Publication Data
US 2018/0169388 A1    Jun. 21, 2018

(51) Int. Cl.
*A61M 25/06* (2006.01)
*A61B 17/34* (2006.01)
*A61M 5/32* (2006.01)
*A61M 25/01* (2006.01)

(52) U.S. Cl.
CPC ......... *A61M 25/0631* (2013.01); *A61B 17/34* (2013.01); *A61B 17/3417* (2013.01); *A61M 25/06* (2013.01); *A61M 5/3243* (2013.01); *A61M 25/0113* (2013.01)

(58) Field of Classification Search
CPC .............. A61M 25/06; A61M 25/0612; A61M 25/0631; A61M 5/3243; A61M 5/322; A61B 17/34; A61B 17/3417
See application file for complete search history.

(56) References Cited

U.S. PATENT DOCUMENTS

| 2007/0185456 A1 | 8/2007 | Nakajima |
| 2011/0288482 A1* | 11/2011 | Farrell ............... A61M 5/326 604/164.04 |
| 2013/0150784 A1* | 6/2013 | Rodriguez Lelis ......... A61M 25/0113 604/110 |

FOREIGN PATENT DOCUMENTS

CN          1660454 A    8/2005

* cited by examiner

*Primary Examiner* — Lauren P Farrar
*Assistant Examiner* — James D Ponton
(74) *Attorney, Agent, or Firm* — Muncy, Geissler, Olds & Lowe, P.C.

(57) ABSTRACT

A manual venous catheter assembly includes a catheter fixing barrel, a catheter provided at the catheter fixing barrel, a puncture needle fixing barrel movably sleeved onto the catheter barrel, a puncture needle fixed to the puncture needle fixing barrel, and a positioning ring base fixed to the puncture needle fixing barrel and surrounding the puncture needle. When the puncture needle fixing barrel moves to an extracted position, the puncture needle is pulled to depart from the catheter, such that the puncture needle is located in the catheter fixing barrel to avoid exposure, and the positioning ring base is abutted and engaged with the catheter fixing barrel to prevent separation between the catheter fixing barrel and the puncture needle fixing barrel, thus achieving the effects of simplifying the structure and facilitating assembly.

9 Claims, 11 Drawing Sheets

MANUAL VENOUS CATHETER ASSEMBLY

BACKGROUND OF THE INVENTION

1. Field of the Invention

The present invention relates generally to medical devices and more particularly, to a manual venous catheter assembly.

2. Description of the Related Art

Intravenous injection is a medical treatment of delivering blood, liquid medicine, nutrient liquid or other medical liquid into the venous. In practice, the intravenous injection can be basically classified into two forms, i.e. transient form and continuous form. The so-called transient intravenous injection (commonly known as injection) is to directly insert a needle into the patient's vein for achieving the effect of infusion. While the continuous intravenous injection (commonly known as the drip-feeding injection) is to insert a venous catheter into the patient's venous first, and then the venous catheter is connected to refillable or replaceable medical liquid for continuously delivering the medical liquid into the patient's body.

In general, the conventional venous catheter assembly is composed of a metal needle and a soft venous catheter sleeved onto the metal needle. In operation, the metal needle and the soft venous catheter are concurrently inserted into the venous by means of the hardness of the metal needle, and then the metal needle is pulled out to leave the soft venous catheter inside the human body, and finally the soft venous catheter is connected to the medical liquid needed by the patient for enabling the soft venous catheter to provide the effect of continuously delivering liquid. After taking out the metal needle, in order to avoid the metal needle from stabbing others, nurses must put a protective jacket on the metal needle before discarding the same. However, during the process of capping the protective jacket, an accident injury caused by the stab of the metal needle may happen due to personal carelessness or unexpected collision caused by an external force. To solve the aforesaid problem, patent No. CN 100536944 discloses a safety venous catheter assembly using a needle sleeve member and an extendable housing unit to cover the whole metal needle. However, the design of multi-layered barrel adopted by the aforesaid patent raises the problems of exceeding structural components and accessories and difficulty in assembly.

SUMMARY OF THE INVENTION

It is a primary objective of the present invention to provide a manual venous catheter assembly, which has a simple structure and is convenient to assemble, thereby increasing convenience in use.

To attain the above-mentioned objective, the present invention provides a manual venous catheter assembly, which comprises: a catheter fixing barrel provided at an end portion with a coupling portion and a first positioning recess adjacent to the coupling portion, and at the other end portion with an outer flange and a second positioning recess adjacent to the outer flange; a catheter detachably sleeved onto the coupling portion of the catheter fixing barrel; a puncture needle fixing barrel movably sleeved onto the catheter fixing barrel in a way that the puncture needle fixing barrel is moveable between an injection position and a retracted position; a puncture needle fixedly mounted to an end portion of the puncture needle fixing barrel; a positioning ring base disposed to the end portion of the puncture needle fixing barrel and surrounding around the puncture needle, the positioning ring base including a stepped stopper portion and at least one resilient positioning piece; wherein when the puncture needle fixing barrel stays at the injection position, the puncture needle is located in the catheter and the resilient positioning piece of the positioning ring base is engaged in the first positioning recess of the catheter fixing barrel; when the puncture needle fixing barrel stays at the retracted position, the puncture needle is departed from the catheter and located inside the catheter fixing barrel, the stepped stopper portion of the positioning ring base is abutted with the outer flange of the catheter fixing barrel, and the resilient positioning piece of the positioning ring base is inwardly retracted and engaged in the second positioning recess of the catheter fixing barrel.

In the technical features of the present invention, the puncture needle fixing barrel comprises an inner cylinder and an outer cylinder surrounding around the inner cylinder to form an axially extending passage between the inner and outer cylinders. The puncture needle fixing barrel is sleeved onto the catheter fixing barrel by means of the axially extending passage. The puncture needle is fixedly mounted to an end of the inner cylinder of the puncture needle fixing barrel. The positioning ring base is fixedly mounted to an end of the outer cylinder of the puncture needle fixing barrel.

In the present invention, the end of the outer cylinder of the puncture needle fixing barrel is provided with an engaging portion, and the positioning ring base is provided with an engaging groove. The engaging portion of the outer cylinder of the puncture needle fixing barrel is engaged with the engaging groove of the positioning ring base.

In the present invention, the outer cylinder of the puncture needle fixing barrel and the positioning ring base are joined together by ultrasonic welding.

In the present invention, the outer cylinder of the puncture needle fixing barrel is provided at an outer peripheral surface thereof with a plurality of anti-slip ribs arranged side by side.

In the present invention, the positioning ring base comprises a hollow groove adjacent to the stepped stopper portion, and the resilient positioning piece is located in the hollow groove and inclinedly extends in a direction from the stepped stopper portion to the catheter.

In the present invention, the catheter comprises a coupling end portion having a tightening ring.

The present invention further comprises a locking ring movably disposed on a barrel body of the catheter fixing barrel. The locking ring has an inner wall surface provided with an internal thread. The catheter comprises a coupling end portion provided with an external thread. When the puncture needle fixing barrel stays at the injection position, the internal thread of the locking ring and the external thread of the catheter are threaded with each other. When the puncture needle fixing barrel stays at the retracted position, the internal thread of the locking ring and the external thread of the catheter are disengaged from each other.

In the present invention, the locking ring includes a first opening and a second opening. The first opening of the locking ring is detachably sleeved onto the coupling end portion of the catheter. The second opening has an inner diameter slightly greater than an outer diameter of the first positioning recess of the catheter fixing barrel.

In the present invention, the first positioning recess of the catheter fixing barrel has an end that is adjacent to the coupling portion and forms a stepped abutment portion. When the first opening of the locking ring is sleeved onto the coupling end portion of the catheter, the locking ring is abutted with the stepped abutment portion of the first positioning recess by means of the second opening.

With the above-mentioned technical features, the advantages of the present invention lie in that: when the puncture needle fixing barrel stays at the injection position, the puncture needle will be located in the catheter to enable the catheter to be inserted into a patient's venous by the hardness of the puncture needle, and the resilient positioning piece of the positioning ring base will be engaged in the first positioning recess of the catheter fixing barrel, such that the resilient positioning piece of the positioning ring base is maintained in an inwardly retracted manner; when the puncture needle fixing barrel stays at the retracted position, the puncture needle will be departed from the catheter and received inside the catheter fixing barrel to prevent exposure, and furthermore the stepped stopper portion of the positioning ring base will be abutted with the outer flange of the catheter fixing barrel to prevent separation between the catheter fixing barrel and the puncture needle fixing barrel, and moreover the resilient positioning piece of the positioning ring base will be inwardly retracted and engaged in the second positioning recess of the catheter fixing barrel to prevent the catheter fixing barrel from being arbitrarily moved by an unexpected external force so as to ensure that the puncture needle is positively maintained inside the catheter fixing barrel.

The present invention is applicable to various medical and health institutions, such as hospitals and clinics.

DETAILED DESCRIPTION OF EMBODIMENTS

Figure 1:
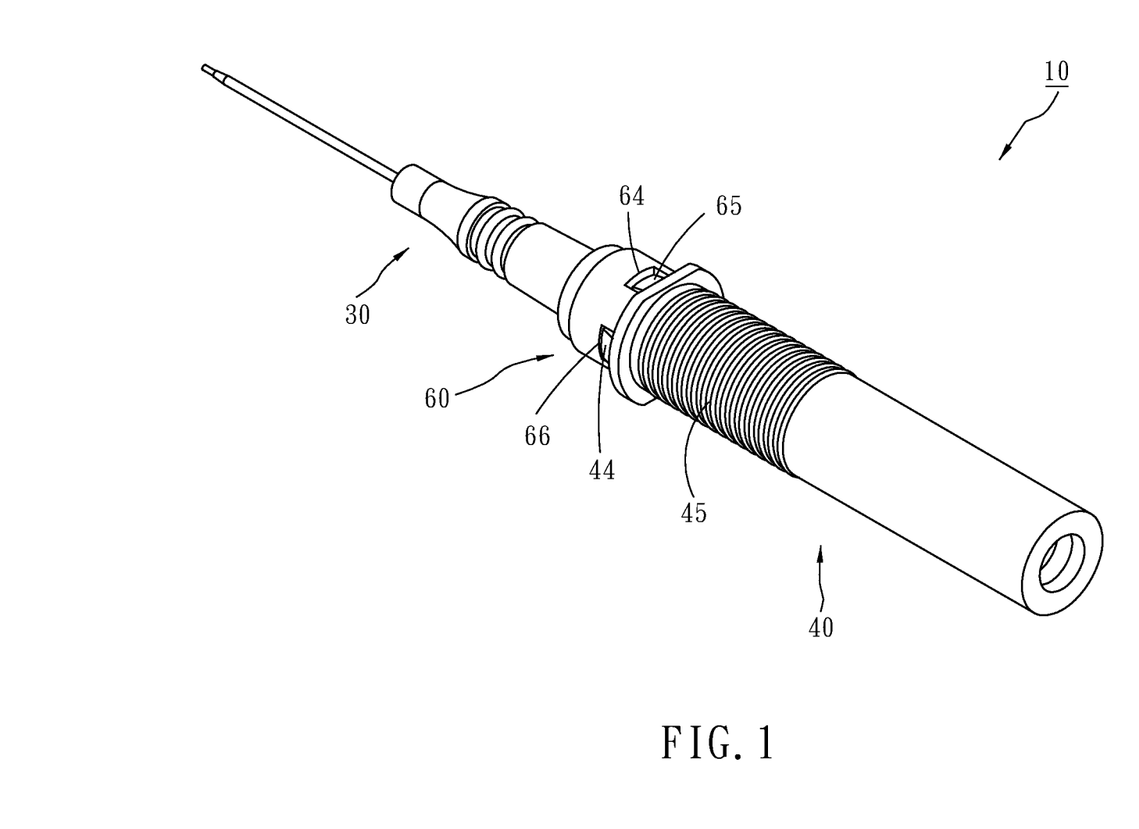
FIG. 1 is a perspective view of the present invention.
Figure 2:
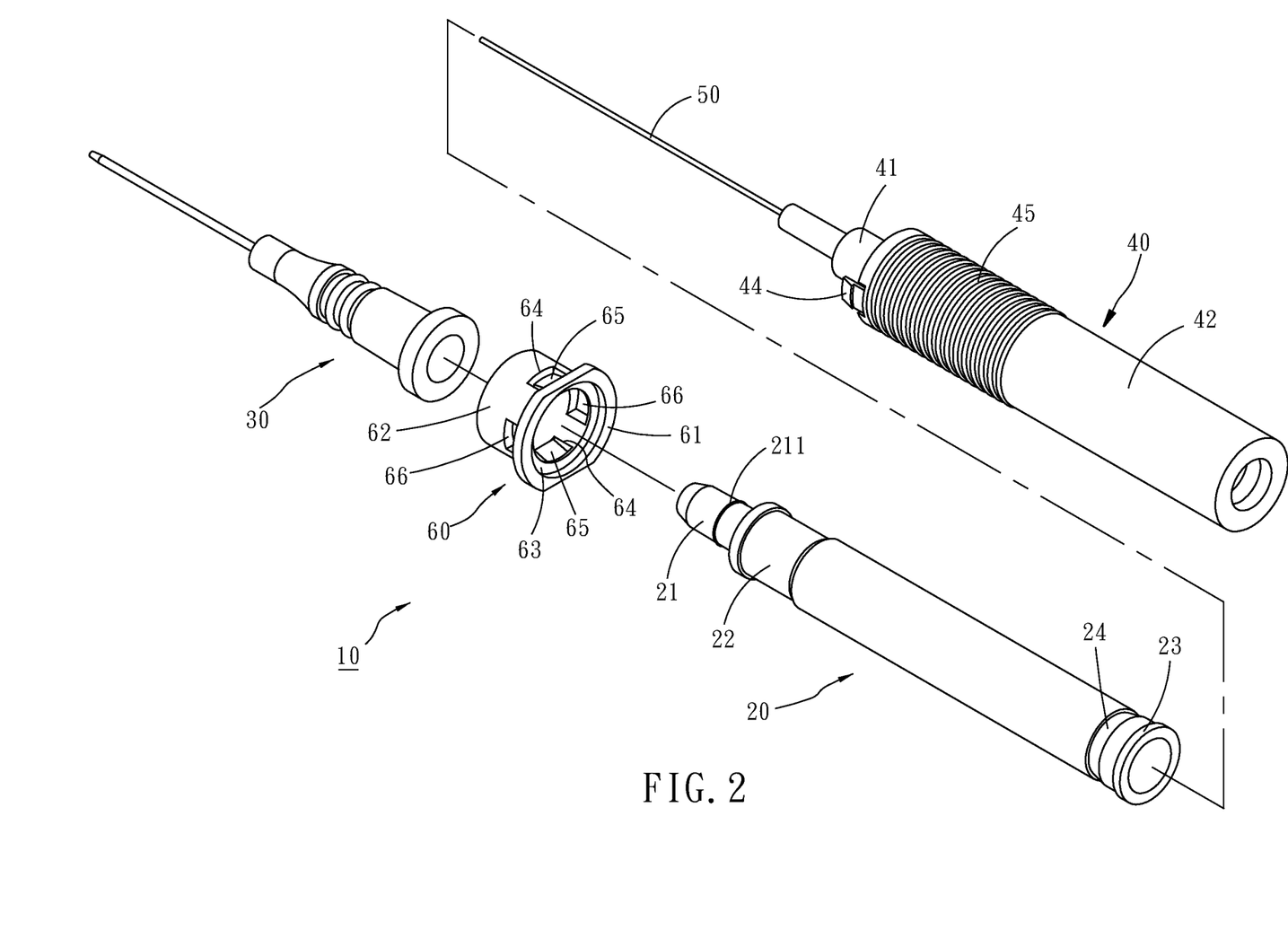
FIG. 2 is an exploded perspective view of the present invention.

Please first refer to FIGS. 1 and 2. The manual venous catheter assembly 10 of the present invention comprises a catheter fixing barrel 20, a catheter 30, a puncture needle fixing barrel 40, a puncture needle 50, and a positioning ring base 60.

An end portion of the catheter fixing barrel 20 has a coupling portion 21 and a first positioning recess 22 adjacent to the coupling portion 21. On the coupling portion 21, a tightening ring 211 is provided. The other end portion of the catheter fixing barrel 20 has an outer flange 23 and a second positioning recess 24 adjacent to the outer flange 23.

The catheter 30 is made of soft material, such as rubber. In assembly, the catheter 30 is sleeved onto the coupling portion 21 of the catheter fixing barrel 20 and retained in position by means of the tightening ring 211, such that the catheter 30 will not easily escape from the coupling portion 21.

Figure 3:
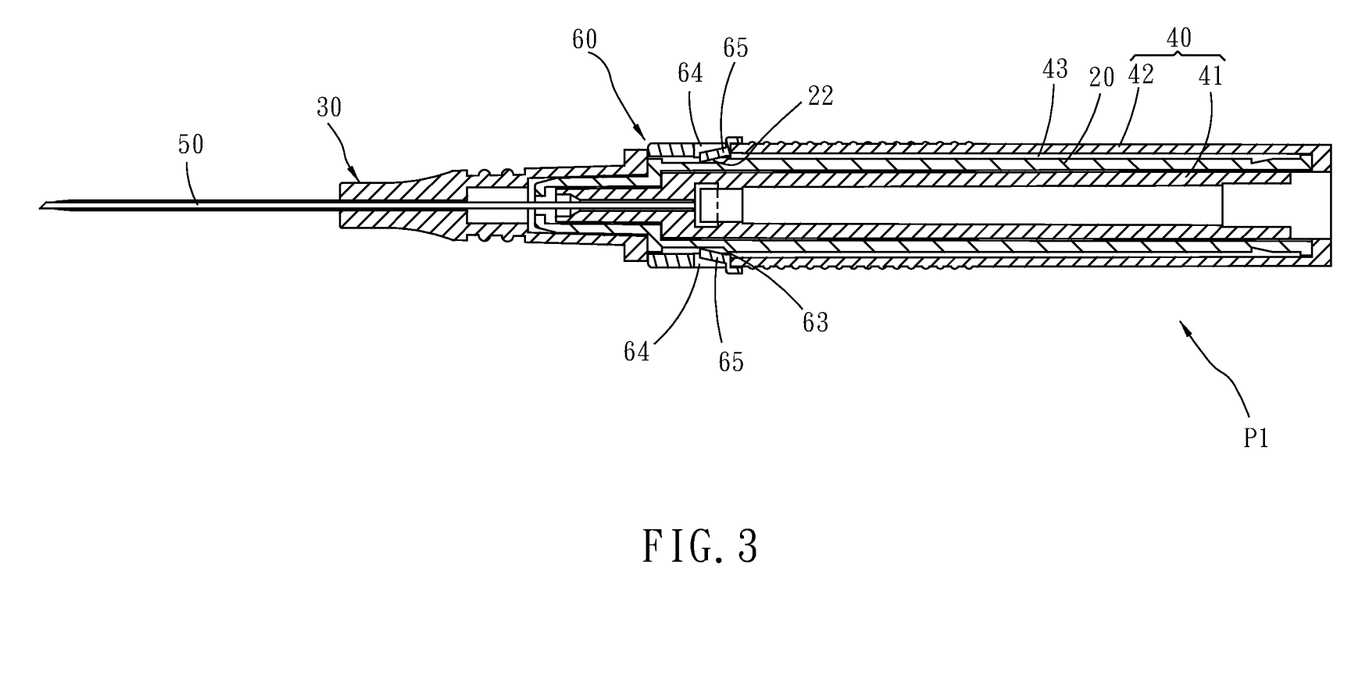
FIG. 3 is a cross-sectional view of the present invention in assembly, mainly showing a state that the puncture needle fixing barrel is located at the injection position.
Figure 4:
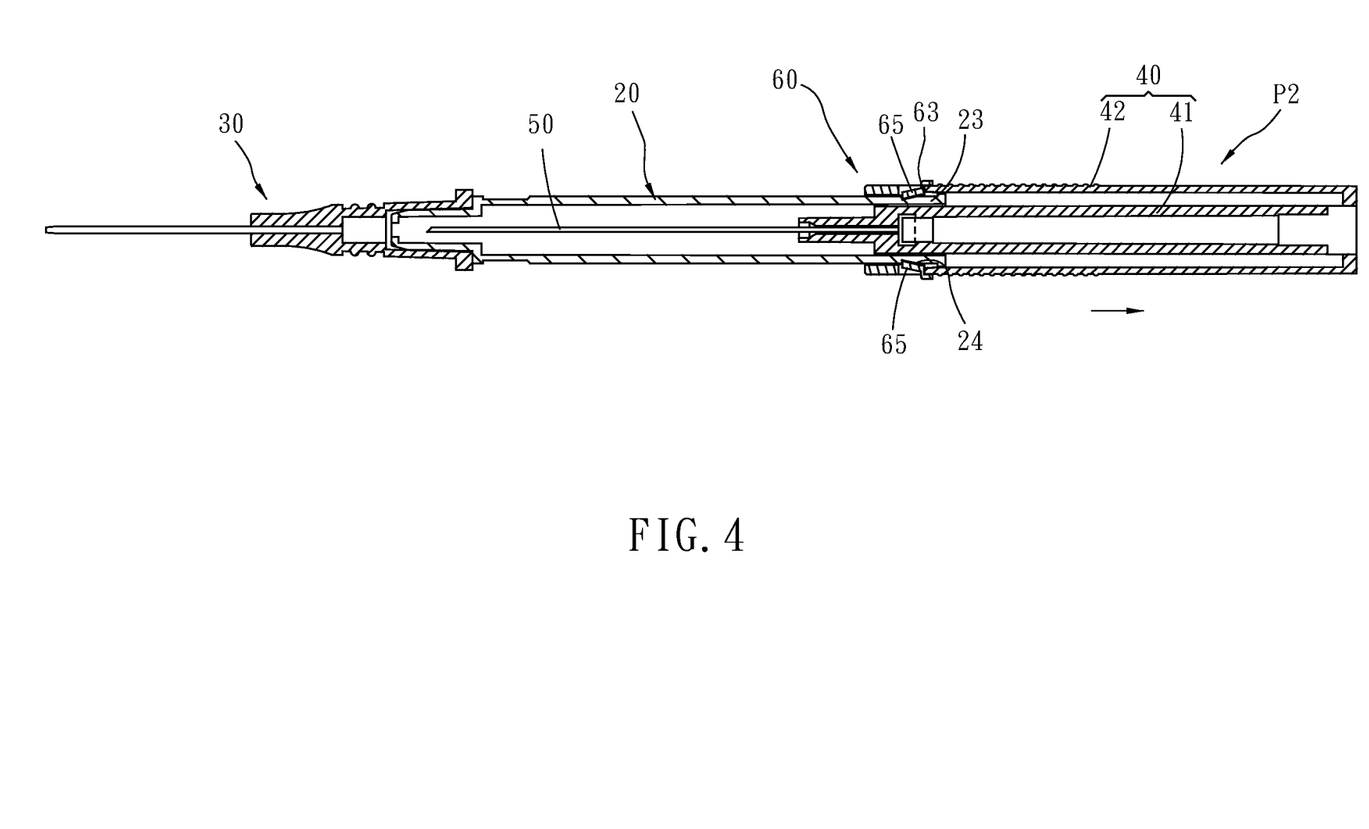
FIG. 4 is similar to FIG. 3, mainly showing a state that the puncture needle fixing barrel is located at the retracted position.

The puncture needle fixing barrel 40 includes an inner cylinder 41 and an outer cylinder 42. As shown in FIGS. 3 and 4, the outer cylinder 42 surrounds around the periphery of the inner cylinder 41 in a way that an axially extending passage 43 is formed between the inner cylinder 41 and the outer cylinder 42. In the process of assembling the puncture needle fixing barrel 40, the puncture needle fixing barrel 40 is sleeved onto the catheter fixing barrel 20 by the axially extending passage 43 in a way that the inner cylinder 41 is received inside the catheter fixing barrel 20 and the puncture needle fixing barrel 40 is moveable relative to the catheter fixing barrel 20 between an injection position P1 and a retracted position P2. Further, as shown in FIG. 2, an end of the outer cylinder 42 of the puncture needle fixing barrel 40 is provided with two opposite engaging portions 44, and an outer peripheral surface of the outer cylinder 42 of the puncture needle fixing barrel 40 is provided with a plurality of anti-slip ribs 45 arranged side by side. The anti-slip ribs 45 are adjacent to the two engaging portions 44.

The puncture needle 50 has an end fixedly mounted to an end of the inner cylinder 41 of the puncture needle fixing barrel 40. When the puncture needle fixing barrel 40 stays at the injection position P1, as shown in FIG. 3, the puncture needle 50 is disposed in the catheter 30. When the puncture needle fixing barrel 40 stays at the retracted position P2, as shown in FIG. 4, the puncture needle 50 is departed from the catheter 30 and received inside the catheter fixing barrel 20.

As shown in FIG. 2, the positioning ring base 60 includes a big diameter ring portion 61 and a small diameter ring portion 62. The big diameter ring portion 61 is connected with an end face of the small diameter ring portion 62 in a way that a stepped stopper portion 63 is formed between the big and small diameter ring portions 61 and 62. The small diameter ring portion 62 has two hollow grooves 64 and two resilient positioning pieces 65. The two hollow grooves 64 are adjacent to the stepped stopper portion 63 and opposite to each other. Each of the two resilient positioning pieces 65 is located in one of the hollow grooves 64 and inclinedly extends in a direction from the stepped stopper portion 63 to the catheter 30, as shown in FIG. 3. As such, when the puncture needle fixing barrel 40 stays at the injection position P1, as shown in FIG. 3, the resilient positioning pieces 65 of the positioning ring base 60 are located in the first positioning recess 22 of the catheter fixing barrel 20. When the puncture needle fixing barrel 40 stays at the retracted position P2, as shown in FIG. 4, the resilient positioning pieces 65 of the positioning ring base 60 are inwardly retracted and engaged in the second positioning recess 24 of the catheter fixing barrel 20. Further, as shown in FIG. 2, the small diameter ring portion 62 of the positioning ring base 60 has two engaging grooves 66 arranged adjacent to the stepped stopper portion 63 and opposite to each other. By means of engaging the two engaging grooves 66 with the two engaging portions 44 of the outer cylinder 42 of the puncture needle fixing barrel 40, the positioning ring base 60 is fixedly mounted to an end of the outer cylinder 42 of the puncture needle fixing barrel 40. It is to be especially mentioned that the positioning ring base 60 may be joined with the outer cylinder 42 of the puncture needle fixing barrel 40 by ultrasonic welding. Under this circumstance, the engaging portions 44 and the engaging grooves 66 can be omitted.

Figure 5:
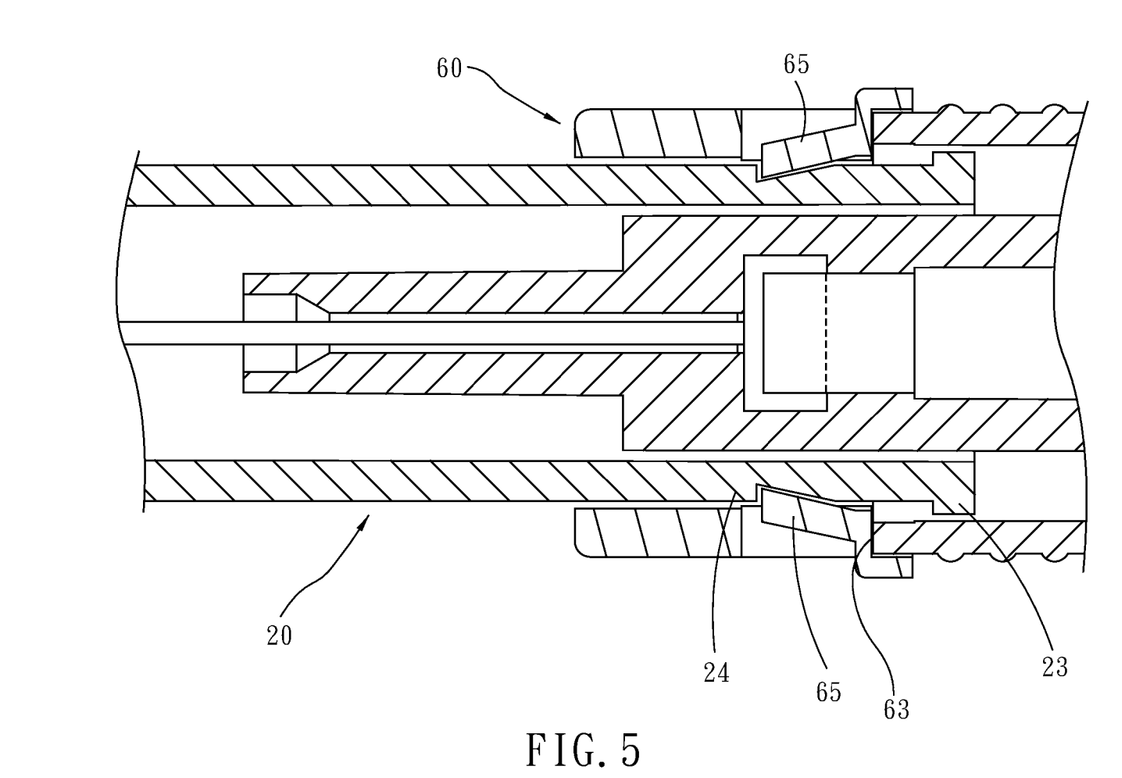
FIG. 5 is a partially enlarged view of FIG. 4.
Figure 6:
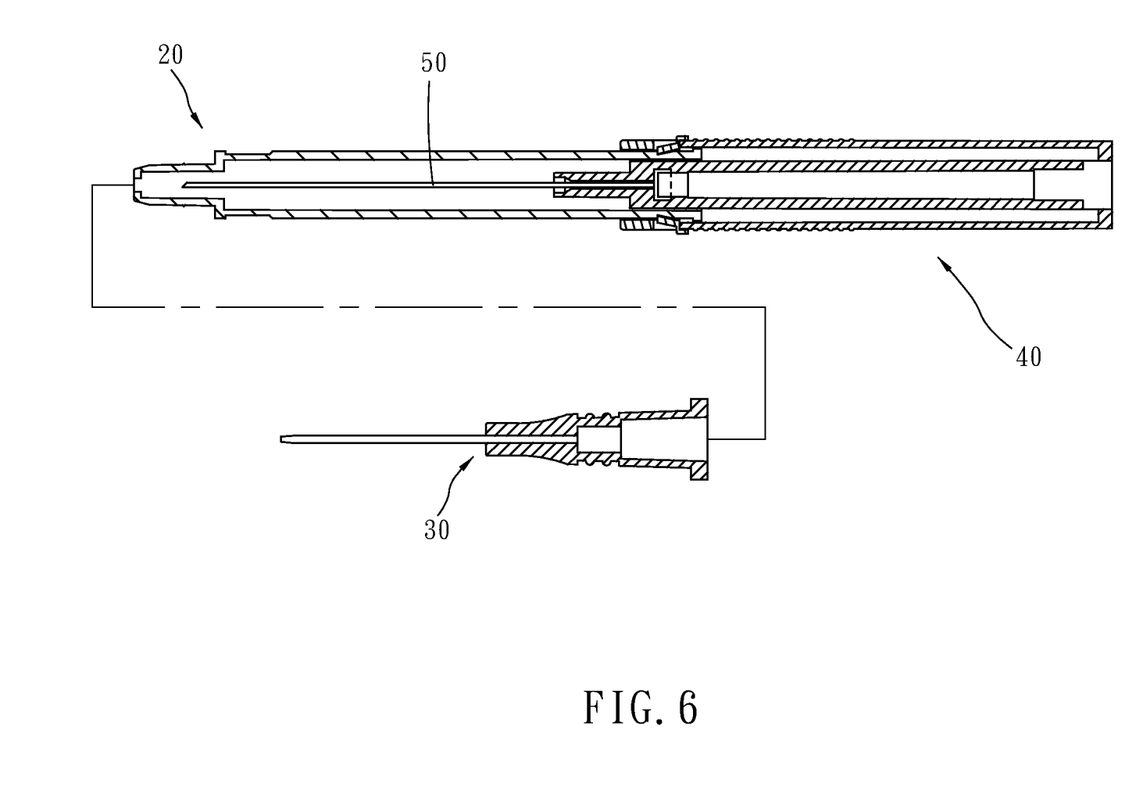
FIG. 6 is similar to FIG. 4, mainly showing a state that the catheter is dismantled from the catheter fixing barrel.
Figure 7:
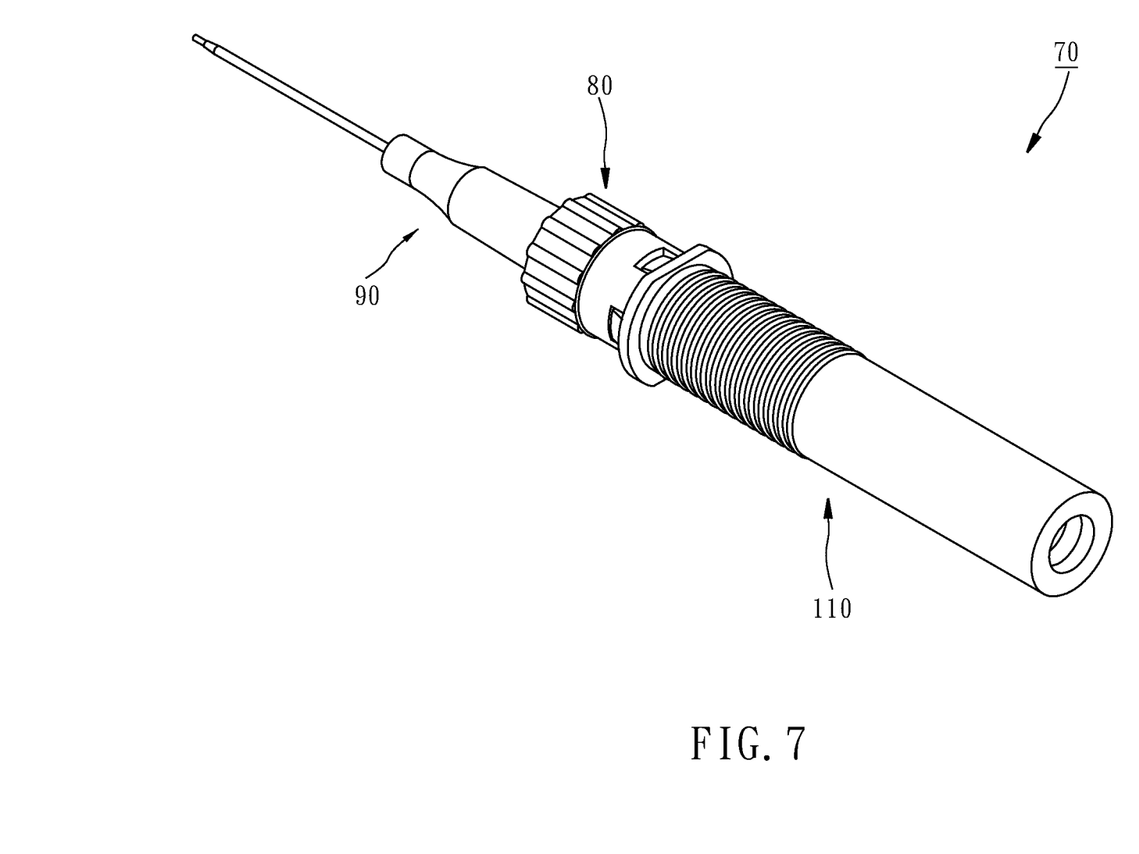
FIG. 7 is a perspective view of another embodiment of the present invention.
Figure 8:
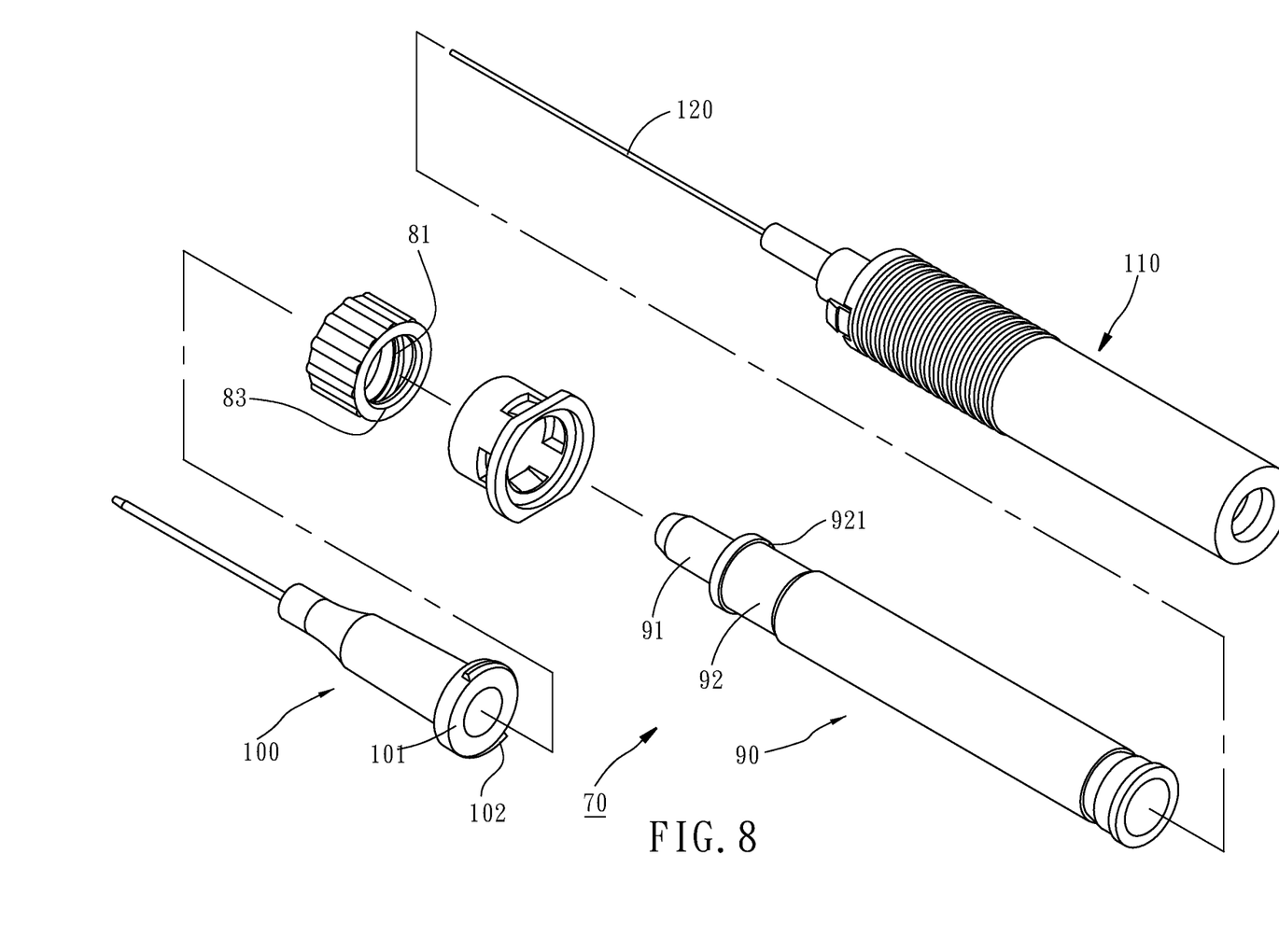
FIG. 8 is an exploded perspective view of another embodiment of the present invention.

It can be learned from the above-disclosed structure that in order to conduct injection, the puncture needle fixing barrel 40 is first maintained at the injection position P1, as shown in FIG. 3, so as to enable the catheter 30 to penetrate through a patient's skin by means of the hardness of the puncture needle 50. At this stage, the resilient positioning pieces 65 of the positioning ring base 60 will be located in the first positioning recess 22 of the catheter fixing barrel 20, so that the resilient positioning pieces 65 are maintained in an inwardly retracted manner. Further, the bottom portion of the catheter fixing barrel 20 will be abutted with the bottom portion of the axially extending passage 43 of the puncture needle fixing barrel 40, such that the puncture needle 50 will not retract back into the catheter 30 during the process of penetrating through the patient's skin. As soon as the catheter 30 is smoothly inserted into the venous, the catheter 30 can be held in position by user's press and the puncture needle fixing barrel 40 is pulled backward to result in that the puncture needle 50, which moves along with the puncture needle fixing barrel 40, will be gradually withdrawn out of the catheter 30, as show in FIGS. 4 and 5, until the stepped stopper portion 63 of the positioning ring base 60 is abutted with the outer flange 23 of the catheter fixing barrel 20, such that the puncture needle fixing barrel is located at the retracted position P2. In the meantime, the resilient positioning pieces 65 of the positioning ring base 60 is compliantly and inwardly retracted and engaged in the second positioning recess 24 of the catheter fixing barrel 20, such that the puncture needle fixing barrel 40 cannot be forwardly moved by push so as to ensure that the puncture needle 50 can be completely received inside the catheter fixing barrel 20 without exposure. Thereafter, the catheter 30 can be separated from the catheter fixing barrel 20, the puncture needle 50 and the puncture needle fixing barrel 40, as shown in FIG. 6, and the catheter 30 indwelled on the patient's body can be further connected with the medical liquid needed by the patient.

In conclusion, by means of the slidable design of the puncture needle fixing barrel 40 in association with the engaging relationship between the resilient positioning pieces 65 of the positioning ring base 60 and the second positioning recess 24 of the catheter fixing barrel 20 and the abutment relationship between the stepped stopper portion 63 of the positioning ring base 60 and the outer flange 23 of the catheter fixing barrel 20, the manual venous catheter assembly 10 of the present invention has a more simplified structure compared to the prior arts. Further, in the process of dismantling the catheter 30, the puncture needle 50 can be retracted and received in the catheter fixing barrel 20 at the same time, thereby achieving the effect of one-step operation. In other words, the present invention is convenient in use, achieving the objective of the present invention.

FIGS. 7 to 11 show another embodiment of the present invention. The manual venous catheter assembly 70 provided by this embodiment is basically the same as the previous embodiment in a majority of structure and components with the differences lying in that the manual venous catheter assembly 70 provided by this embodiment further comprises a locking ring 80 movably disposed on a barrel body of the catheter fixing barrel 90. The locking ring 80 has an internal thread 81, a first opening 82, and a second opening 83. The first positioning recess 92 of the catheter fixing barrel 90 has an end that is adjacent to the coupling portion 91 and forms a stepped abutment portion 921. The catheter 100 includes a coupling end portion 101 provided with an external thread 102. The internal thread 81 is provided at an inner wall surface of the locking ring 80. The first opening 82 of the locking ring 80 is detachably sleeved onto the coupling end portion 101 of the catheter 100 to enable that the internal thread 81 of the locking ring 80 and the external thread 102 of the catheter 100 can be threaded with each other. The second opening 82 of the locking ring 80 has an inner diameter slightly greater than an outer diameter of the first positioning recess 92 of the catheter fixing barrel 90, such that the movement of the locking ring 80 is restricted within the first positioning groove 92.

Figure 9:
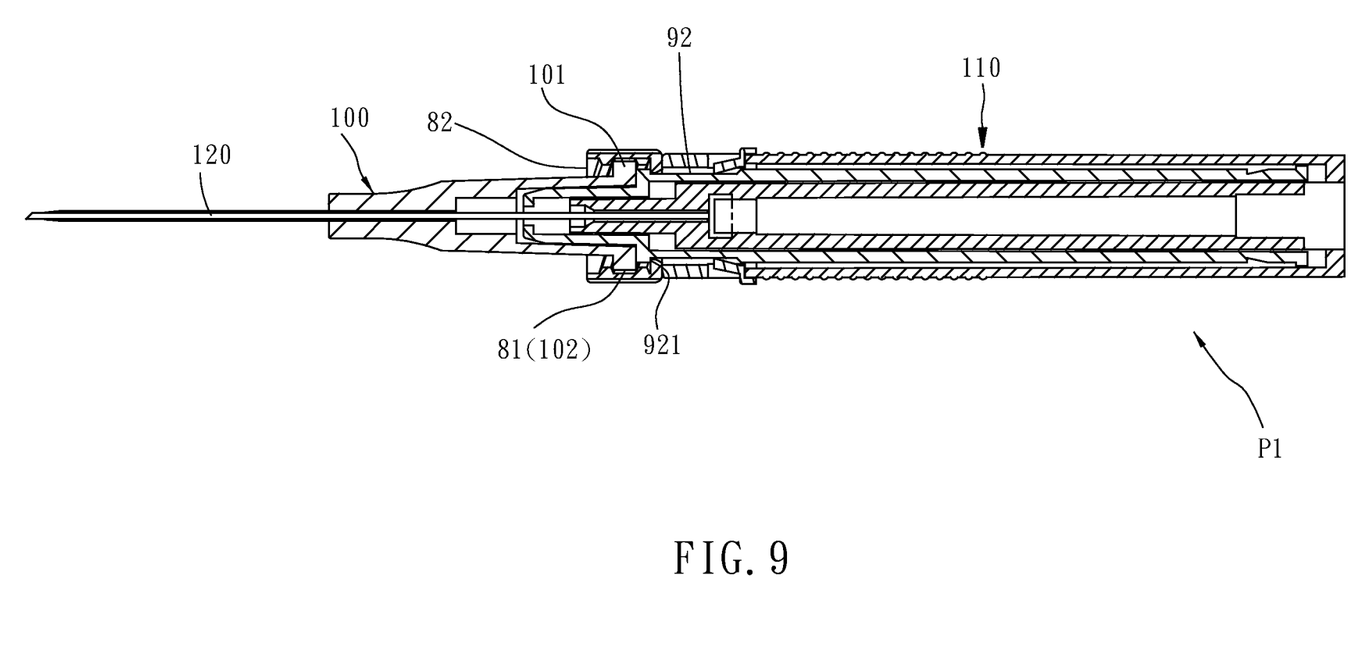
FIG. 9 is a cross-sectional view of another embodiment of the present invention in assembly, mainly showing a state that the puncture needle fixing barrel is located at the injection position.
Figure 10:
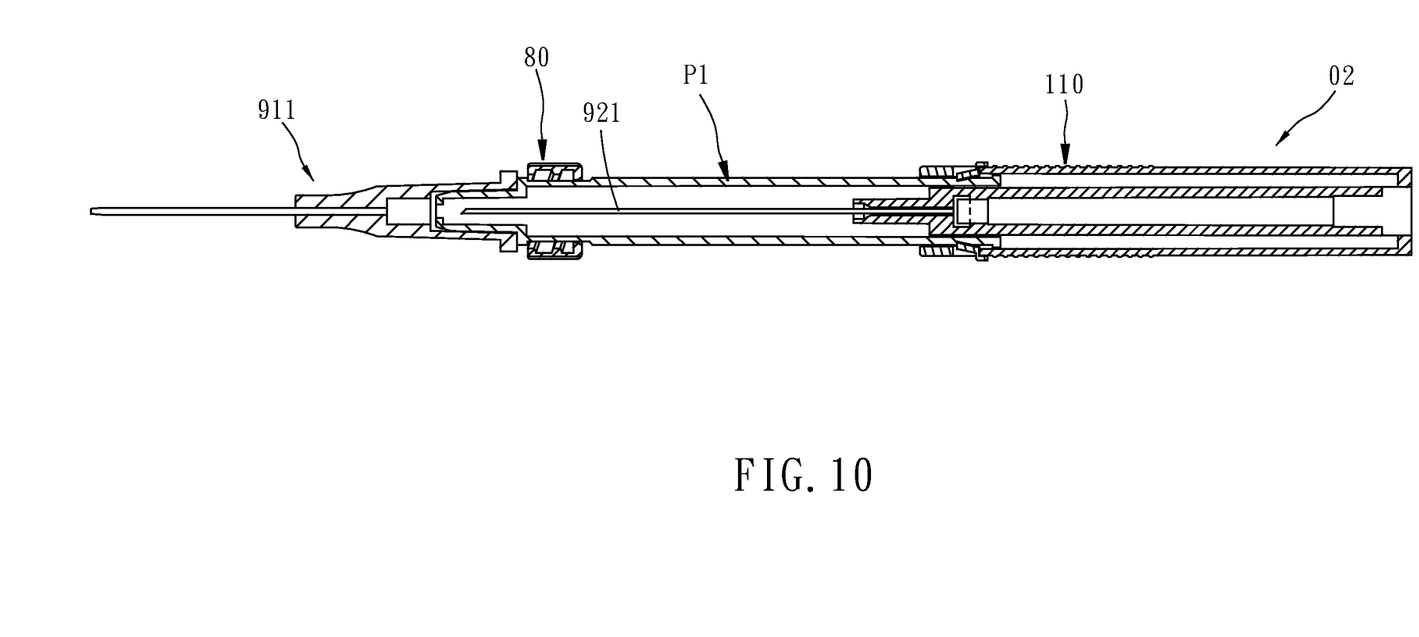
FIG. 10 is similar to FIG. 9, mainly showing a state that the puncture needle fixing barrel is located at the retracted position.
Figure 11:
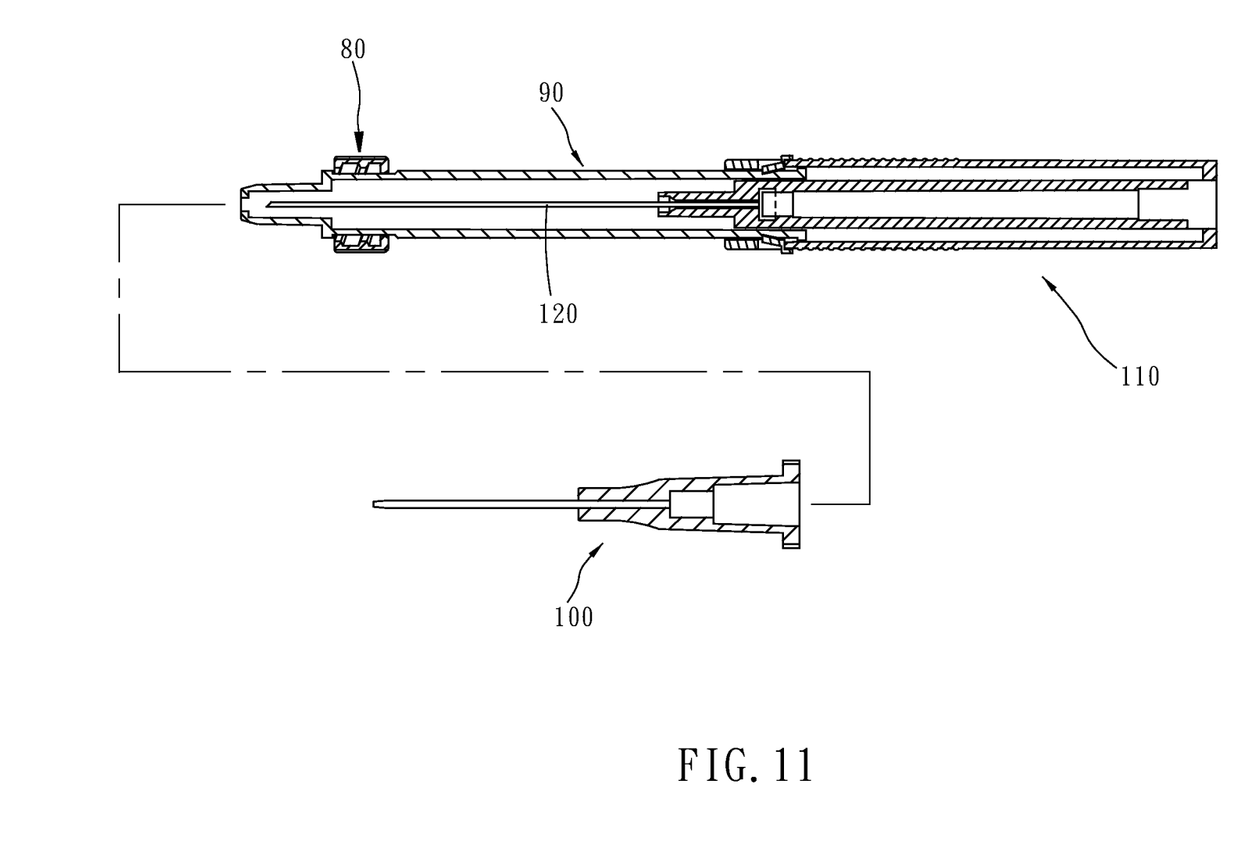
FIG. 11 is similar to FIG. 10, mainly showing a state that the catheter is dismantled from the catheter fixing barrel.

By means of the above-mentioned structure, when the puncture needle fixing barrel 110 stays at the injection position P1, as shown in FIG. 9, the locking ring 80 is abutted with the stepped abutment portion 921 of the first positioning recess 92 of the catheter fixing barrel 90, which is adjacent to the coupling portion 91, by means of the second opening 83, and the first opening 82 of the locking ring 80 is sleeved onto the coupling end portion 101 of the catheter 100 in a way that the internal thread 81 of the locking ring 80 and the external thread 102 of the catheter 100 are threaded with each other, such that the catheter 100 is fixed with the coupling portion 91 of the catheter fixing barrel 90. As a result, the puncture needle 120 will not retract into the catheter 100 during the process of penetrating through the patient's skin. When the puncture needle fixing barrel 110 is located at the retracted position P2, the internal thread 81 of the locking ring 80 can be disengaged from the external thread 102 of the catheter 100 by simply turning the locking ring 80. As long as the internal thread 81 of the locking ring 80 is disengaged from the external thread 102 of the catheter 100, the catheter 100 can be dismantled from the catheter fixing barrel 90, as shown in FIG. 11. With the features of this embodiment, the catheter 100 can be stably fixed in position.

INDUSTRIAL APPLICABILITY

The invention provides a manual venous catheter assembly suitable for being used in various medical and health institutions, and has very broad prospects in industrial application.

What is claimed is:

1. A manual venous catheter assembly, comprising:
  a catheter fixing barrel provided at an end portion with a coupling portion and a first positioning recess adjacent to the coupling portion, and at an other end portion with an outer flange and a second positioning recess adjacent to the outer flange;
  a catheter detachably sleeved onto the coupling portion of the catheter fixing barrel;
  a puncture needle fixing barrel movably sleeved onto the catheter fixing barrel in a way that the puncture needle fixing barrel is moveable between an injection position and a retracted position;
  a puncture needle fixedly mounted to an end portion of the puncture needle fixing barrel;
  a positioning ring base disposed on the end portion of the puncture needle fixing barrel and surrounding the puncture needle, the positioning ring base including a stepped stopper portion and at least one resilient positioning piece;
  wherein when the puncture needle fixing barrel is at the injection position, the puncture needle is located in the catheter and the resilient positioning piece of the positioning ring base is engaged in the first positioning recess of the catheter fixing barrel; when the puncture needle fixing barrel is at the retracted position, the puncture needle is departed from the catheter and located inside the catheter fixing barrel, the stepped stopper portion of the positioning ring base is abutted with the outer flange of the catheter fixing barrel, and the resilient positioning piece of the positioning ring base is inwardly retracted and engaged in the second positioning recess of the catheter fixing barrel;

wherein the puncture needle fixing barrel comprises an inner cylinder and an outer cylinder surrounding the inner cylinder to form an axially extending passage between the inner and outer cylinders; the puncture needle fixing barrel is sleeved onto the catheter fixing barrel in the axially extending passage; the puncture needle is fixedly mounted to an end of the inner cylinder of the puncture needle fixing barrel; the positioning ring base is fixedly mounted to an end of the outer cylinder of the puncture needle fixing barrel.

2. The manual venous catheter assembly as claimed in claim 1, wherein the end of the outer cylinder of the puncture needle fixing barrel is provided with an engaging portion, and the positioning ring base is provided with an engaging groove; the engaging portion of the outer cylinder of the puncture needle fixing barrel is engaged with the engaging groove of the positioning ring base.

3. The manual venous catheter assembly as claimed in claim 1, wherein the outer cylinder of the puncture needle fixing barrel and the positioning ring base are joined together by ultrasonic welding.

4. The manual venous catheter assembly as claimed in claim 1, wherein the outer cylinder of the puncture needle fixing barrel is provided at an outer peripheral surface thereof with a plurality of anti-slip ribs arranged side by side.

5. The manual venous catheter assembly as claimed in claim 1, wherein the positioning ring base comprises a hollow groove adjacent to the stepped stopper portion, and the resilient positioning piece is located in the hollow groove and inclinedly extends in a direction from the stepped stopper portion to the catheter.

6. The manual venous catheter assembly as claimed in claim 1, wherein the catheter comprises a coupling end portion having a tightening ring.

7. The manual venous catheter assembly as claimed in claim 1, further comprising a locking ring movably disposed on a barrel body of the catheter fixing barrel; the locking ring has an inner wall surface provided with an internal thread; the catheter comprises a coupling end portion provided with an external thread; when the puncture needle fixing barrel is at the injection position, the internal thread of the locking ring and the external thread of the catheter are threaded with each other; when the puncture needle fixing barrel is at the retracted position, the internal thread of the locking ring and the external thread of the catheter are disengaged from each other.

8. The manual venous catheter assembly as claimed in claim 7, wherein the locking ring includes a first opening and a second opening; the first opening of the locking ring is detachably sleeved onto the coupling end portion of the catheter; the second opening of the locking ring has an inner diameter slightly greater than an outer diameter of the first positioning recess of the catheter fixing barrel.

9. The manual venous catheter assembly as claimed in claim 8, wherein the first positioning recess of the catheter fixing barrel has an end that is adjacent to the coupling portion and forms a stepped abutment portion; when the first opening of the locking ring is sleeved onto the coupling end portion of the catheter, the locking ring is abutted with the stepped abutment portion of the first positioning recess by the second opening.

\* \* \* \* \*